United States Patent [19]
Rygaard

[11] Patent Number: 5,725,544
[45] Date of Patent: Mar. 10, 1998

[54] METHOD AND INSTRUMENT FOR ESTABLISHING THE RECEIVING SITE OF A CORONARY ARTERY BYPASS GRAFT

[75] Inventor: Jorgen A. Rygaard, Gentofte, Denmark

[73] Assignee: Oticon A/S, Hellerup, Denmark

[21] Appl. No.: 663,133
[22] PCT Filed: Apr. 12, 1994
[86] PCT No.: PCT/DK94/00148
§ 371 Date: Aug. 22, 1996
§ 102(e) Date: Aug. 22, 1996
[87] PCT Pub. No.: WO95/17127
PCT Pub. Date: Jun. 29, 1995

[30] Foreign Application Priority Data

Dec. 23, 1993 [DK] Denmark .................. 1455/93

[51] Int. Cl.$^6$ .................................................. A61F 17/00
[52] U.S. Cl. ........................................ 606/167; 128/898
[58] Field of Search ............................ 606/167, 170, 606/171, 159; 128/898

[56] References Cited

U.S. PATENT DOCUMENTS

| 5,119,983 | 6/1992 | Green et al. |
| 5,158,222 | 10/1992 | Green et al. |
| 5,254,120 | 10/1993 | Cinberg et al. ................... 606/170 |
| 5,285,944 | 2/1994 | Green et al. |

Primary Examiner—Michael Buiz
Assistant Examiner—Kevin Truong
Attorney, Agent, or Firm—Larson & Taylor

[57] ABSTRACT

A method of locating a constriction in a coronary artery and performing an arteriotomy distally thereof which comprises locating the site of a constriction in a coronary artery by scanning the artery with a non-invasive sensing instrument capable of detecting the constriction. The sensing instrument has associated therewith a cutting instrument comprised of a cutter and member for moving the cutter into a position for making an incision. After the constriction is located, the cutting member is moved into a cutting position distal of the constriction and an incision is made through the wall of the artery into the lumen thereof.

3 Claims, 6 Drawing Sheets

METHOD AND INSTRUMENT FOR ESTABLISHING THE RECEIVING SITE OF A CORONARY ARTERY BYPASS GRAFT

TECHNICAL FIELD

The present invention relates to a method for locating an arterial constriction and performing an arteriotomy distally thereof, especially with a view to establishing a connection between the root of the aorta and a selected part of a coronary artery, such as set forth in the preamble of claim 1.

BACKGROUND ART

Modern heart surgery was developed fundamentally in the nineteen-fifties together with the extra-corporeal circulation, based on the use of the heart-and-lung machine, making it possible to replace heart valves and to correct certain congenital heart disorders; this as a whole was designated "open heart surgery", as the heart itself, its ventricles and internal functional parts were opened during the operation.

As a natural extension of this method, the coronary bypass surgery emerged in the mid-sixties, also based on the use of the same per-operative technology, viz. the heart-and-lung machine. In this case the surgeon, although not having to operate within the heart itself, needed peace to work in the operating field, i.e. the "coronary tree", the heart's own circulatory system, substantially embedded in the surface of the heart in the form of two main stems—right and left— gradually branching out down along the heart, finally to end deep below the surface in the form of the end-arterial branches of the heart musculature.

Thus, the techniques already established by the use of the heart-and-lung machine was taken over directly, although the coronary bypass operation could not be categorized as "open heart surgery", but rather as "closed heart surgery"— simply to have peace and quiet in the operating field.

The use of the heart-and-lung machine involves a trauma to the heart itself, and more or less serious complications will often appear post-operatively, during intensive care as well as later; thus, in short, a so-called post-perfusion syndrome has been described.

DISCLOSURE OF THE INVENTION

It is the object of the present invention to provide a method of the kind referred to above, with which it is possible to perform the initial steps of a coronary bypass connection safely, quickly and accurately and without having to use extra-corporeal circulation, and this object is achieved with a method of said kind, which according to the present invention comprises the steps set forth in the characterizing clause of claim 1. By proceeding in this manner, the initial steps of the coronary bypass operation, comprising locating the constriction and performing the arteriotomy needed for the subsequent anastomosis, may be performed on the beating heart.

The invention also relates to an instrument for carrying out the method referred to above, and according to the invention this instrument comprises the features set forth in the characterizing clause of claim 4.

Advantageous embodiments of the method and instrument, the effects of which are explained in more detail in the following detailed portion of the present description, are set forth in claims 2, 3 and 5, respectively.

BRIEF DESCRIPTION OF THE DRAWINGS

In the following detailed portion of the present description, the invention will be explained in more detail with reference to the drawings, in which.

DESCRIPTION OF THE PREFERRED EMBODIMENTS

In the following part of the present description, two surgical instruments will be described and their methods of use explained, viz.:

I. A sensing and incising instrument and its method of use, and

II. an anastomosis instrument and its method of use.

The instrument and method according to I are the subject of the claims in the present application, whereas the instrument and method according to II are the subject of the claims in the co-pending application WO 94/ . . . (B, S & Co. Ref. No. 53135).

I. Sensing and incising instrument

Figure 1:
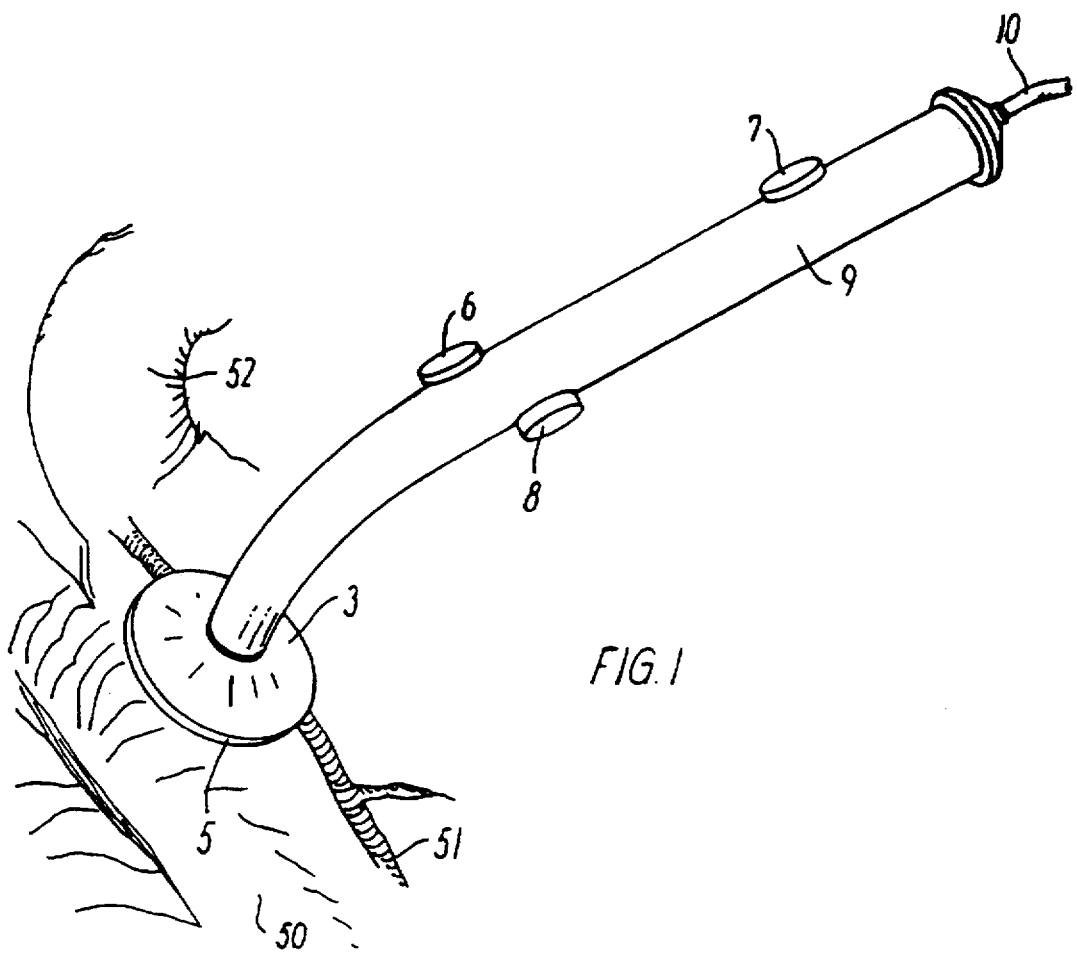
FIG. 1 is a simplified perspective view of a sensing and incising instrument with its sensing means placed in contact with a coronary artery and the surrounding surface of the heart.
Figure 2:
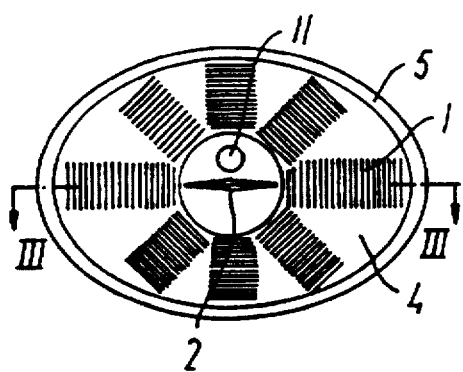
FIG. 2 shows a first face on the instrument of FIG. 1, comprising said sensing means.
Figure 3:
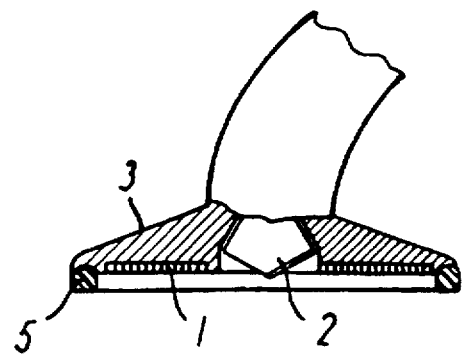
FIG. 3 is a sectional view along the line III—III in FIG. 2, FIG. 4 at a greatly enlarged scale and in longitudinal section shows an anastomotic instrument prepared for carrying out an end-to-side anastomosis in an incision in the coronary artery made by the sensing and incising instrument shown in FIG. 1.

The combined sensing and incising instrument shown in FIGS. 1–3 comprises a head 3 secured to a handle 9. The head 3 is shaped like a flat or slightly curved or dished disk, the front face 4 of which faces away from the handle 9 with a view to be able to be brought into contact with the external surface of a heart 50 and a coronary artery 51 supplying part of the heart muscle with blood from the aorta 52.

The front face 4 carries two highly important components, viz. an ultrasonic probe 1 and a knife 2.

The ultrasonic probe 1, shown in FIGS. 2 and 3 symbolically and purely as an example as a composite array of individuel ultrasonic transducers, is in a manner known per se adapted to transmit ultrasonic probing signals into living tissue and to receive reflected signals, cooperating with an external signal processing and display unit (not shown) to produce a screen image corresponding to a transverse and/or longitudinal sectional view of the tissue concerned, at the same time displaying other information, such as preferably the flow velocity of blood flowing through arteries shown in sectional view. The probe 1 may be based on the use of the Doppler principle, such as is well known in the art of non-invasive examination of living tissue. The ultrasonic probe 1 is connected to the external unit through suitable conductors in a cable 10, the latter also comprising a vacuum conduit mentioned below.

The knife 2 is placed centrally of the probe 1 and is oriented in a direction enabling it to make an incision extending in the longitudinal direction of the coronary artery 51 when the latter also is shown in longitudinal cross-sectional view by the display unit cooperating with the ultrasonic probe 1. The knife 2 is operated by means of a knife button 8. The knife button 8 may, in a manner not shown, be slidably supported on the handle 9, so as to make the knife protrude from the front face 4 or, in a rest position, to recede behind it. Alternatively, the knife 2 may be constituted by a remotely-controlled cutter or a laser cutter, suitably controlled by the knife button 8. Persons skilled in the art of making surgical instruments will know how to establish a suitable connection.

A vacuum aperture 11 in the front face 4 is connected to a vacuum source (not shown) through a vacuum conduit in the cable 10, and controlled by a vacuum-on button 6, operable to connect the vacuum aperture 11 to said vacuum conduit so as to aspirate air from the front face 4, and a vacuum-off button 7, operable to connect the vacuum aperture 11 to atmosphere so as to release any vacuum established in front of the front face 4, all in a manner to be explained below.

The front face 4 is surrounded by a soft sealing lip 5 making it possible to establish a sealed space between on the one hand the external wall of the heart 50 and the coronary artery 51 and on the other hand the front face 4 of the head 3.

II. Anastomosis instrument

The anastomosis instrument with an auxiliary fitting shown in FIGS. 4–11 comprises a tube 20, one end of which is cut off at an angle of the order of approx. 60° with the longitudinal axis 25, thus forming an oblique end face 21. Adjoining the end face 21 is an internal circumferential recess 22, the function of which will be explained below. Within the tube 20 is a slidably supported tubular ejector 23, the end face 24 of which will, according to the position of the ejector 23, lie clear of the recess 22 (cf. FIG. 4) or have been moved into the bounds of the recess 22 (cf. FIG. 8), for a purpose to be explained below. The ejector 23 is preferably spring-biased against a stop in a manner not shown to the position shown in FIG. 4, from which position it may be moved towards the position shown in FIG. 8 by operating an ejecting flange 26 on its opposite end. The ejector 23 is formed so as to allow a substantial space around the longitudinal axis 25 of the tube 20, for reasons to become apparent.

The anastomotic fitting 30 shown in FIGS. 4, 5 and 7–11 consists of an elastically flexible brace 31, bent so as to enable its free ends to cross each other, and provided with a number of outwardly protruding spikes 32. The spikes at the "rear end", i.e. the end pointing to the right in the drawing, are directed obliquely outwardly and towards the "front end", this obliqueness being reduced gradually towards said "front end". The purpose of this arrangement will become apparent below.

III. Methods of using the above instruments I and II

As already described in the introductory part of the present specification, the invention is related to cardiac surgery of the kind normally referred to as "coronary bypass surgery". As is well known, this type of surgery comprises establishing a new connection between the aorta ascendens and the coronary artery below, i.e. downstream of, a stenosis or occlusion having been located by a preceding diagnosis.

The purpose of establishing this extra connection is, of course, to bypass a constriction in the coronary artery, said constriction constituting a well-known pathological condition, the causes and effects of which need not be discussed in the present context.

According to a combination of the present invention and the invention subject of said co-pending application No. WO 94/ . . . (B. S & Co. Ref. No. 53135), coronary bypass surgery of the kind referred to above is carried out in the manner described below.

After having made the patient ready for surgery in any suitable manner, the thorax is opened mid-sternally so as to provide access to the front side of the heart 50 as indicated in FIG. 1. Then, the coronary artery 51 being suspected of having a constriction is identified, after which the front face 4 of the head 3 is brought into contact with the coronary artery 51 concerned and the immediately surrounding surface of the heart 50 so as to make the ultrasonic probe 1 cover the artery and with the knife 2 in the receding position ready for making an incision in the artery. The artery 51 is scanned by moving the head 3 lengthwise and crosswise of it, until, by watching the image or images on the display unit, a location is found, in which the knife 2 is in position facing the coronary artery 51 immediately downstream of a constriction of the kind referred to above. It should be noted that during this brief sensing operation, the heart 50 is beating, thus causing the surface, against which the front face 4 abuts, to move rhythmically, but in a "drug-controlled" manner. In order to hold the head 3 with the front face 4 temporarily in position with the probe 1 covering the coronary segment below the constriction, the vacuum-on button 6 is now operated to apply vacuum to the space bounded by the front face 4, the surface of the heart 50 and the coronary artery 51, sealed by the sealing lip 5 surrounding the front face 4.

With the vacuum applied, the head 3 will remain in exactly the same position, temporarily attached by suction to the surface of the heart 50, the latter—of course—still beating, and during such attachment the knife 2 is held in said position in readiness for making the incision in the coronary artery 51.

At a suitable moment in time, such as the peak of the diastole, the knife button 8 is operated to bring the knife 2 to make the incision, thus producing an arteriotomy, after which the vacuum is rapidly released by operating the vacuum-off button 7, upon which the instrument is removed and the arteriotomy temporarily closed, such as by holding a finger tip against it, so as to avoid or reduce bleeding.

When the sensing and incising instrument shown in FIG. 1 has been removed from the heart, an end-to-side anastomosis is performed as soon and rapidly as possible by using the anastomosis instrument shown in FIGS. 4–10 in conjunction with—of course—a graft vessel and an anastomotic fitting as described above.

After having established an anastomosis between one end of the graft vessel and the arteriotomy in the coronary artery 51 in a manner to be described in more detail below, the opposite end of the graft vessel is suitably prepared and connected to the aorta, such as in the conventional manner of previously known coronary bypass surgery.

Before establishing an end-to-side anastomosis between said first end, i.e. the distal end, of the graft vessel, certain simple preparatory work must be done by "loading" the anastomosis instrument shown in FIGS. 4–10 with the graft vessel and anastomotic fitting.

Figure 4:
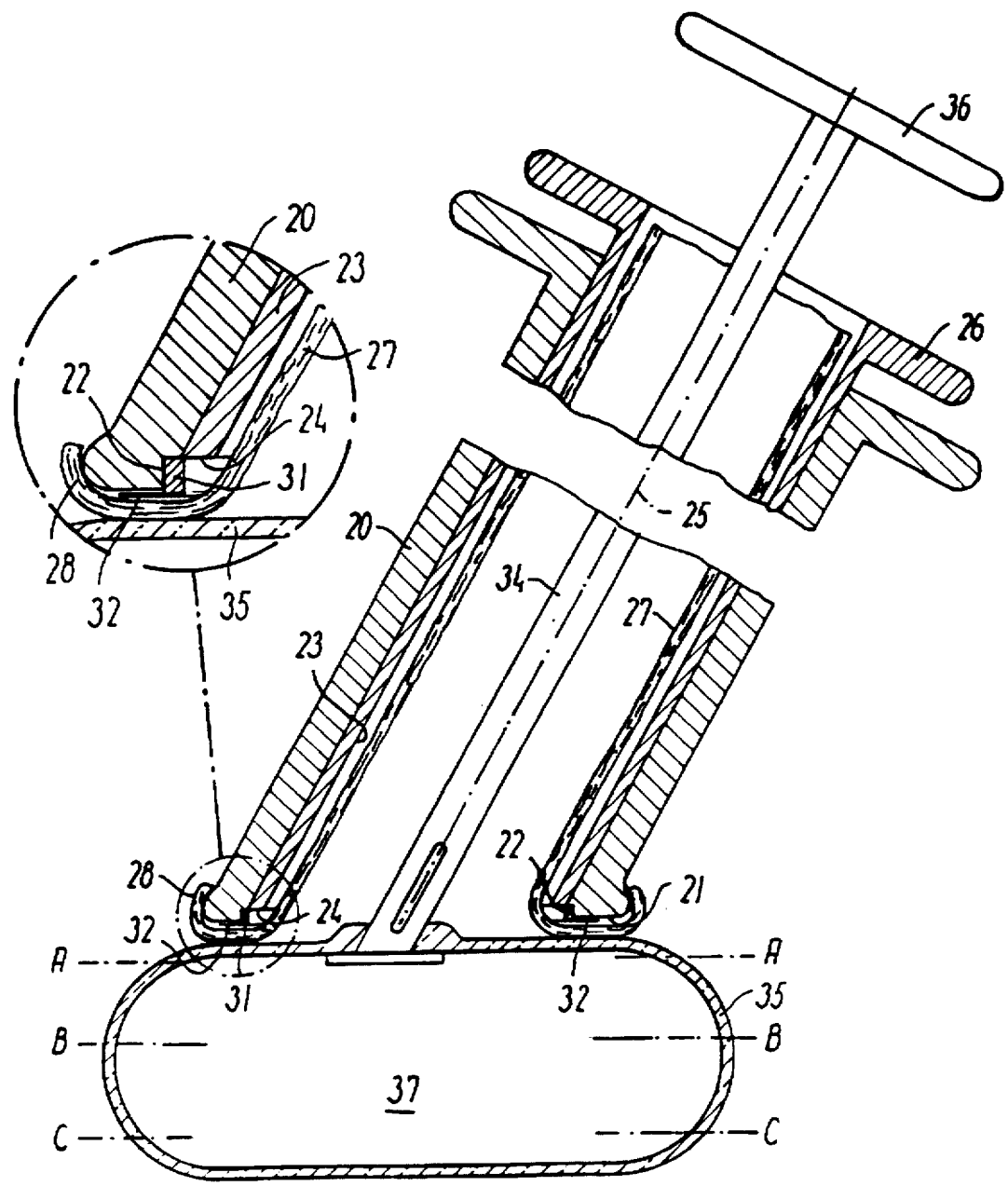

The steps in the preparatory work are as follows:

I. it is ensured that the ejector 23 is in the withdrawn position shown in FIG. 4, II. an anastomotic fitting, such as the fitting 30, is bent elastically inwards sufficiently for its brace 31 to fit into the circumferential recess 22 with the spikes 32 protruding in front of the end face 21 on the tube 20, after which the fitting is released so as to retain itself in engagement with the recess 22 by its own elastic force.

Figure 5:
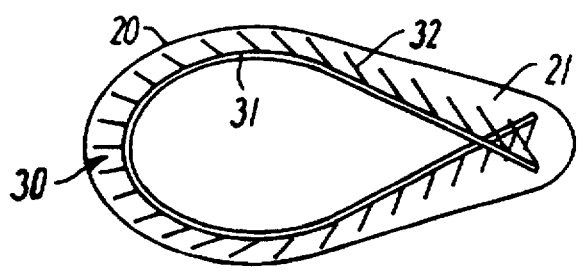
FIG. 5 is a simplified bottom view of certain parts of the instrument shown in FIG. 4.
Figure 6:
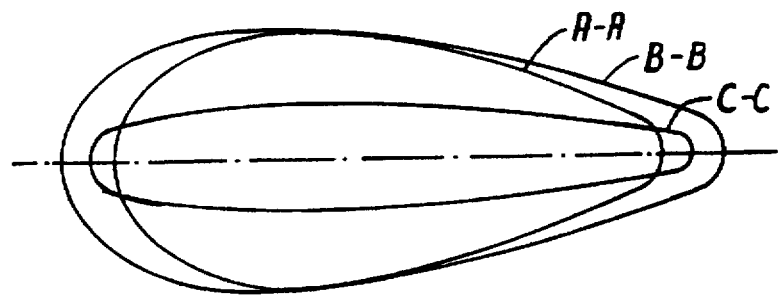
FIG. 6 is a set of contour curves illustrating the shape of a part of the instrument shown in FIG. 4, FIGS. 7–10 show the "front end" of the instrument shown in FIG. 4 during various stages of the operation in carrying out an end-to-side anastomosis.

III. a bypass vessel (of natural or artificial origin) 27 is inserted through the anastomotic fitting 30 into the passage inside the ejector 23 and the tube 20, cf. FIG. 4, and the free end of the vessel is everted about the fitting 30 and the end face 21 of the tube 20 so as to form a collar 28 about the end of the tube 20, thus making the intima on the collar 28 face outwardly. Then, a guiding device comprising a rod 34 with a guide body 35 of a "streamlined" shape, cf. also FIG. 6 in conjunction with FIG. 5, is inserted into the tube 20 inside the graft vessel 27 and provided with a detachable push-button 36 at the opposite end. The guide body 35 is made of soft elastic flexible material and comprises a cavity 37 filled with a heparin solution, the purpose of which will become apparent. The anastomosis instrument is now "loaded" and ready to be used for establishing an end-to-side anastomosis with the coronary artery 51.

It will appear obvious that this work of "loading" the anastomosis instrument should have been completed before locating the constriction and making the incision in the coronary artery 51 in the manner described above. Preferably, steps I and II are carried out by the manufacturer, as only step III, entailing work with the sensitive graft vessel 27, will have to be carried out in the operating theatre.

Figure 7:
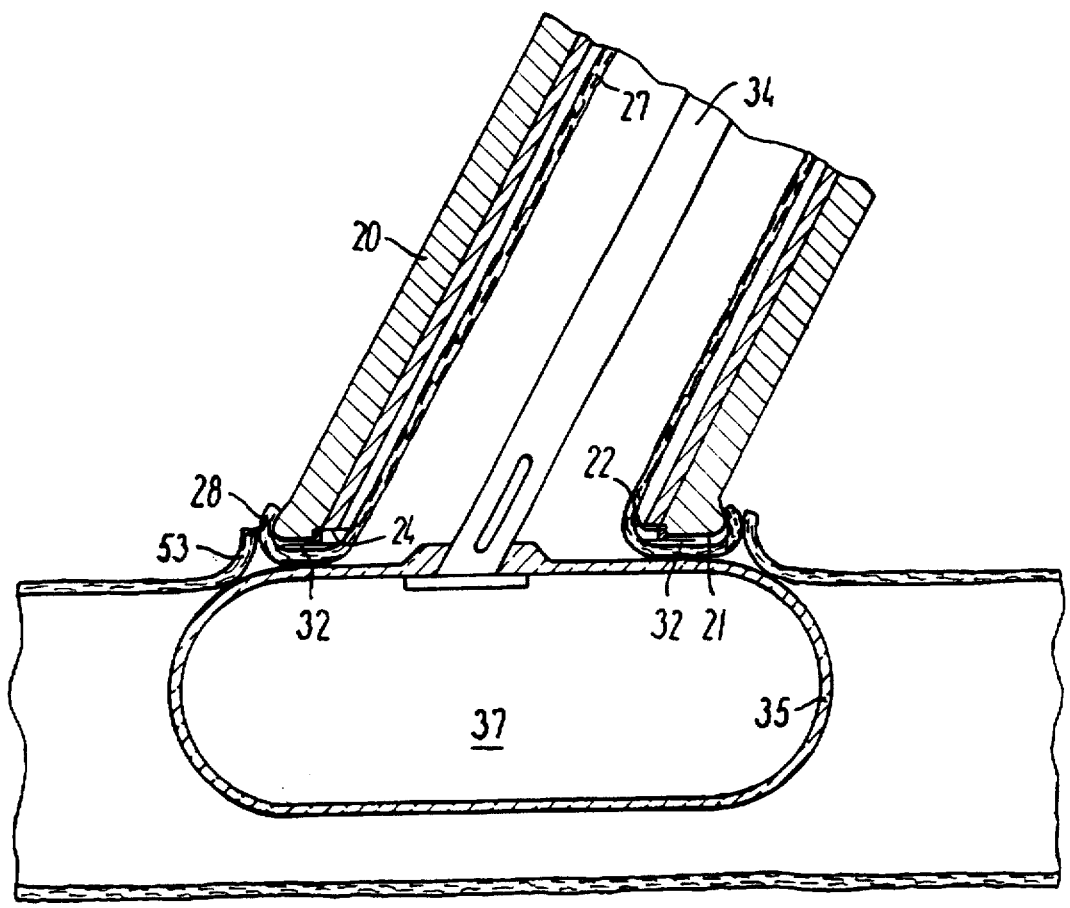

The finger or whatever object has been used for temporarily closing the incision made in the coronary artery 51 by the knife 2 is now removed, and the tube 20, "loaded" with the bypass vessel 27, is now inserted into the incision and manoeuvred in a manner to make the intima facing outwardly of the collar 28 contact the intima on the wall region 53 bounding the incision, cf. FIG. 7. This step is facilitated by the guide body 35, causing the formation of a "waistline" around its upper part and the everted part of the graft vessel 27 forming the collar 28. The wall region 53 around the incision, being elastic and slippery, will slip into this "waistline" into the position shown in FIG. 7. In this manner, the tube 20 will have been manoeuvred into a relative position, in which the spikes 32, if the brace 30 is released, will penetrate both the collar 28 and the wall region 53.

Figure 8:
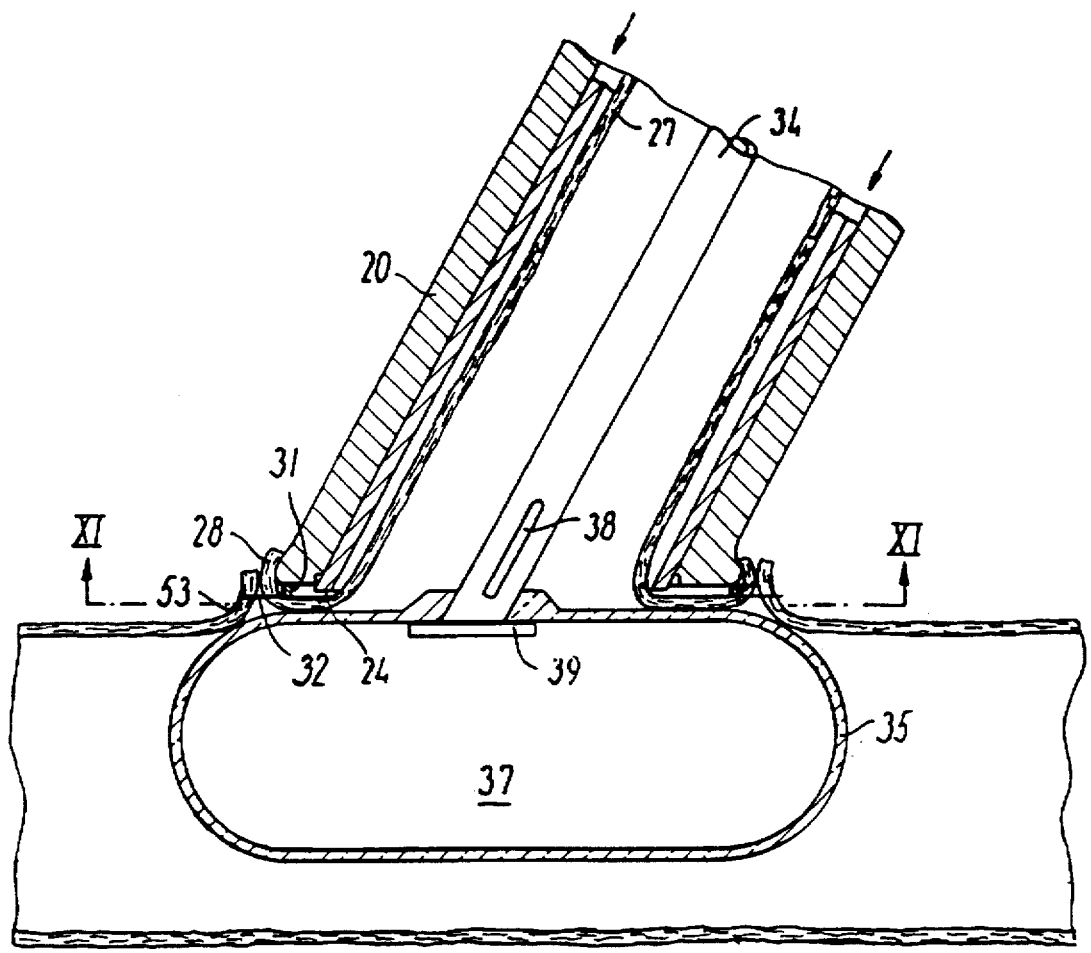
Figure 9:
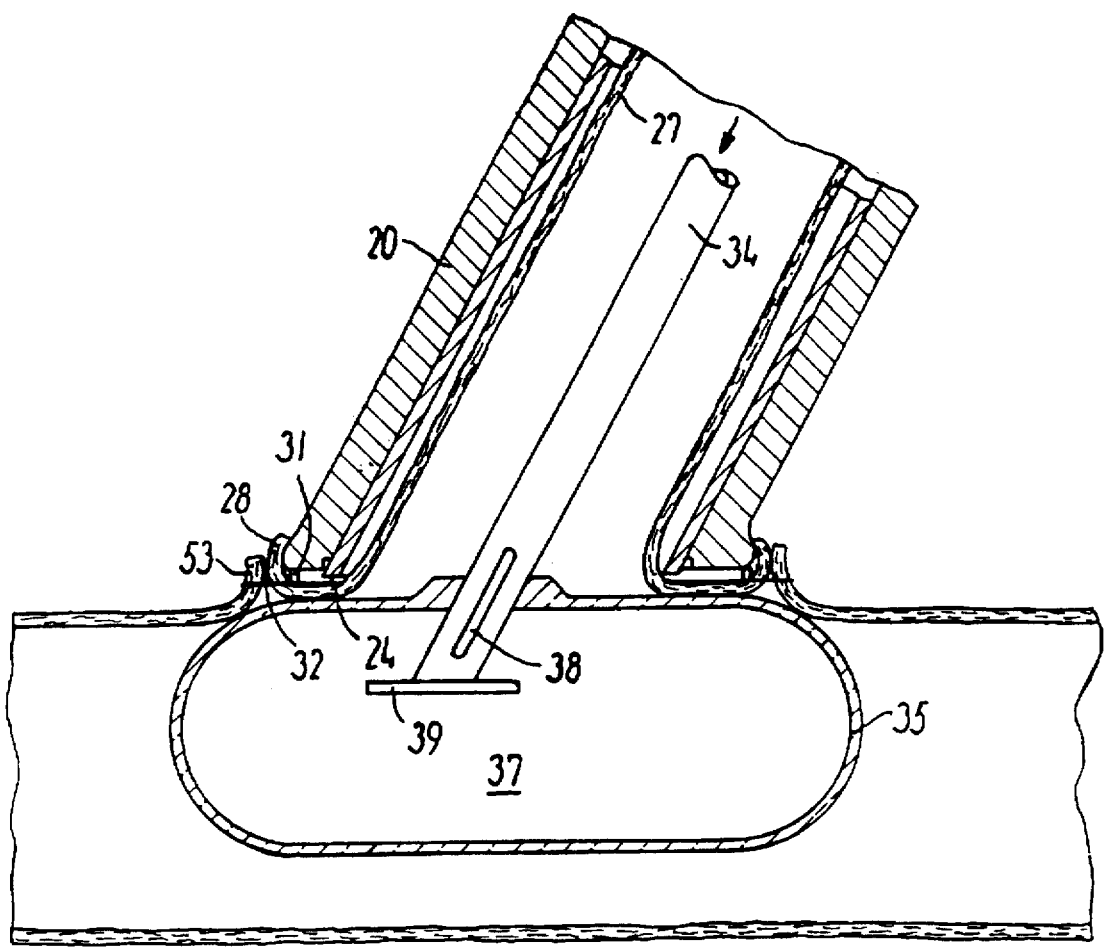
Figure 11:
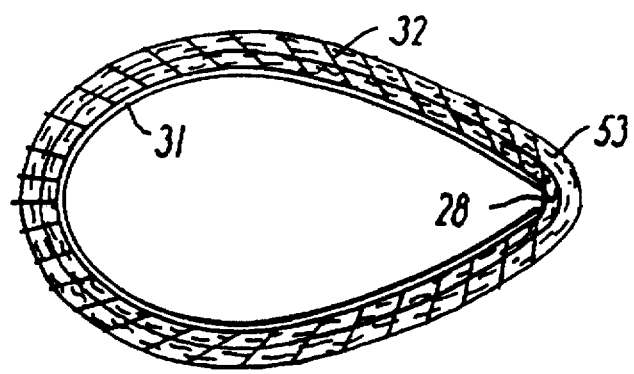
FIG. 11 is a sectional view along the line XI—XI in FIG. 8, reduced to showing only the parts of the vessels concerned having been "nailed together".

The ejector 23 is now operated by pressing the ejecting flange 26 downwards, thus moving the ejector end face 24 to the position shown in FIG. 8, during this movement pushing the brace 31 out of the recess 22, thus making it free under the elastic force, with which it has been held in the recess 22, to move rapidly outwardly so as to penetrate the collar 28 and the wall region 53 as shown in FIG. 8, thus joining these two parts in an intima-to-intima fashion. As the spikes 32 at the "rear end" of the brace 31 are directed obliquely outwards and towards the "front end", the whole brace 30 will be pushed forward, when the oblique spikes penetrate the tissues, so that the spikes at the "front end" will also be made to penetrate the tissues in that region. As indicated in FIG. 11, a small gap at the "rear end" may remain "unstitched", but—due to intima-to-intima agglutination—with a minimum of leakage or none at all. In practice this will not cause any problems, as any possible bleeding through this gap will rapidly be stopped and the gap sealed automatically by natural self-coagulation of the blood.

Figure 10:
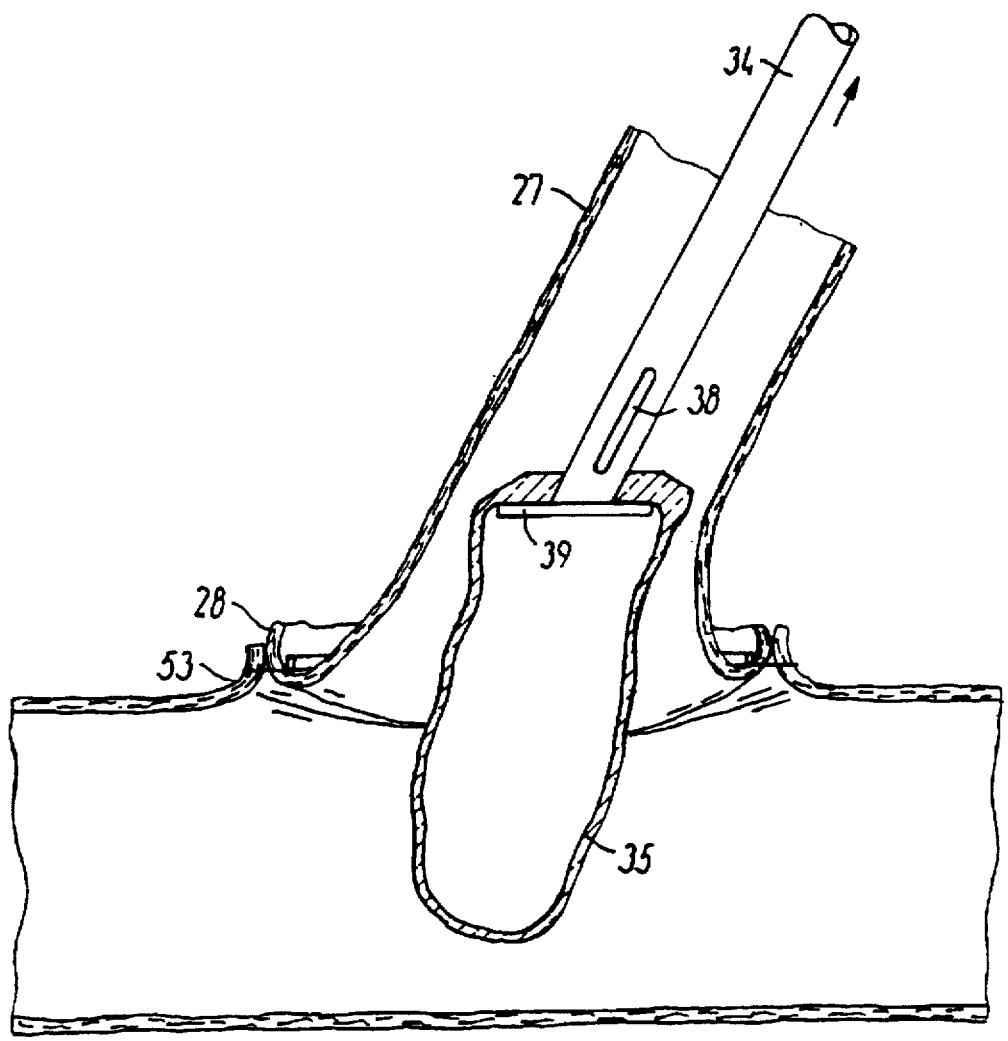

The tube 20 with the ejector 23, the rod 34 and the guide body 35 must now be removed. This is carried out by first pushing the push-button 36 downwards, so that a head 39 on the opposite end of the rod 34 is moved away from the opening on the top wall of the guide body 35, through which the rod 34 extends. Further downward movement of the rod 34 causes a groove 38 close to the lower end of the rod to enter the opening, thus establishing communication between the cavity 37 and the lumen of the graft vessel 27. The heparin solution in the cavity 37 will now flow into the lumen of the graft vessel 27, and at the same time, the guide body 35, until now having been held elastically distended to the shape shown in FIGS. 5 and 6 by the solution, will collapse. At this stage, the tube 20 with the ejector 23 is removed by pulling them away from the anastomosis, after which, as shown in FIG. 10, the collapsed guide body 35 is pulled out through the graft vessel 27, the head 39 preventing the rod 34 from being pulled out of the guide body 35.

Now, the opposite end of the bypass vessel 27 is joined to the aorta in any suitable conventional manner, thus completing the bypass connection desired.

LIST OF PARTS

1 Ultrasonic probe
2 Knife
3 Head
4 Front face
5 Sealing lip
6 Vacuum-on button
7 Vacuum-off button
8 Knife button
9 Handle
10 Cable
11 Vacuum aperture
20 Tube
21 End face
22 Circumferential recess
23 Ejector
24 Ejector end face
25 Longitudinal axis
26 Ejecting flange
27 Bypass vessel
28 Collar
30 Anastomotic fitting
31 Brace
32 Spike
34 Rod
35 Guide body
36 Push-button
37 Cavity
38 Groove
39 Head
50 Heart
51 Coronary artery
52 Aorta
53 Wall region

I claim:

1. A method of locating a constriction in a coronary artery and performing an arteriotomy distally thereof which comprises locating the site of a constriction in a coronary artery having a lumen therein by scanning said artery with a non-invasive sensing instrument capable of detecting said constriction, said sensing instrument having associated therewith a cutting instrument comprised of a cutter and means for moving said cutter into a position for making an incision, and after locating said constriction, moving said cutting member into a cutting position distal of said constriction and making an incision through the wall of said artery into the lumen thereof.

2. A method according the claim 1 wherein the non-invasive sensing instrument and said cutting instrument used to locate said constriction and make said incision constitute a combined sensing and cutting instrument.

3. A method according to claim 2 wherein the combined sensing or cutting instrument further comprises a holding means capable of being activated and inactivated for holding the instrument in abutment with an external surface of the heart such that the cutter can be activated to form an incision in the coronary artery.

* * * * *